(12) United States Patent
Bastien

(10) Patent No.: US 10,267,767 B2
(45) Date of Patent: Apr. 23, 2019

(54) NON-DESTRUCTIVE INSPECTION HAVING PHASE AMPLITUDE MODULATION WITH TIME DIVISION MULTIPLEXING

(71) Applicant: Gaspard Bastien, Quebec (CA)

(72) Inventor: Gaspard Bastien, Quebec (CA)

(73) Assignee: OLYMPUS SCIENTIFIC SOLUTIONS AMERICAS INC., Waltham, MA (US)

(*) Notice: Subject to any disclaimer, the term of this patent is extended or adjusted under 35 U.S.C. 154(b) by 232 days.

(21) Appl. No.: 15/499,986

(22) Filed: Apr. 28, 2017

(65) Prior Publication Data

US 2017/0315096 A1 Nov. 2, 2017

Related U.S. Application Data

(60) Provisional application No. 62/328,778, filed on Apr. 28, 2016.

(51) Int. Cl.
| | | |
|---|---|---|
| *G01N 27/90* | (2006.01) | |
| *G01R 25/00* | (2006.01) | |
| *H03L 7/081* | (2006.01) | |
| *H04B 3/30* | (2006.01) | |
| *H04L 25/49* | (2006.01) | |

(52) U.S. Cl.
CPC ......... *G01N 27/9046* (2013.01); *G01R 25/00* (2013.01); *H03L 7/081* (2013.01); *H04B 3/30* (2013.01); *H04L 25/4917* (2013.01)

(58) Field of Classification Search
CPC .... G01N 27/90; G01N 27/9046; G01N 29/32; G01N 29/4463; G01N 29/449; G01N 27/902; G01N 27/9033
See application file for complete search history.

*Primary Examiner* — Alesa Allgood
(74) *Attorney, Agent, or Firm* — C. Tricia Liu; Robert Kaim

(57) ABSTRACT

A combination of pulse-amplitude modulation and time division multiplexing is used to increase the scan speed when performing non-destructive inspection, such as with an eddy current array.

18 Claims, 4 Drawing Sheets

NON-DESTRUCTIVE INSPECTION HAVING PHASE AMPLITUDE MODULATION WITH TIME DIVISION MULTIPLEXING

CROSS-REFERENCE TO RELATED APPLICATIONS

This application claims the benefit and priority of U.S. Provisional patent application Ser. No. 62/328,778, filed Apr. 28, 2016, entitled INCREASED SPEED AND REDUCED NOISE IN EDDY CURRENT INSPECTION, the entire disclosure of which is incorporated herein by reference.

FIELD OF THE INVENTION

The invention relates in general to use of non-destructive inspection devices, such as eddy current probes, and in particular to improving the speed of inspection using phase amplitude modulation (PAM) with time division multiplexing (TDM).

BACKGROUND OF THE INVENTION

Note that the present disclosure is described in terms of a preferred embodiment of the invention for use with eddy current probes. However, the applicability of the invention is not limited to eddy current probes, and all applications of the invention to other types of non-destructive inspection probes, such as ultrasonic probes, are within the scope of the present disclosure.

Eddy Current (EC) is a commonly used method for non-destructive testing and inspection (NDT/NDI). Eddy Current Array (ECA) probes use multiple sensors in order to increase the inspection coverage. Using multiple excitation coils and receiving coils (sensors) allows the user to inspect a given surface faster than with a single EC sensor. Array probes using up to 32 sensors are not uncommon. However, due to constraints of size and cost, most ECA instruments have a limited number of electronic sensing inputs. For example, it is common for a compact hand-held ECA instrument to have as few as 4 electronic inputs for as many as 64 sensors. In such a case, an analog multiplexer is used to switch between multiple sensors at each electronic input.

FIG. 1A shows an example in existing practice of a multiplexer 4' which has eight input channels from a sensor array 2', allowing data from up to eight sensors to be acquired with a single electronic sensing module 10'. Sensing module 10' comprises an amplifier 6' and a digitizer 8'.

A common method of achieving multiplexing is known in the art as Time Division Multiplexing (TDM). TDM is a method of transmitting and receiving independent signals over a common signal path by means of synchronized switches which cause each signal to appear on the line for only a fraction of time in an alternating pattern. An ECA instrument would thus sample every sensor in such a way that the input signals from each sensor are periodically sampled, with each sensor being allocated a time slot equal to the period of the signal. FIG. 2A shows an example of a sinusoidal excitation signal, scanning through four input sensors with four sequential time slots each having a duration equal to the period of the excitation signal. It is understood that the signal pattern shown in FIG. 2A is repeated, thereby repeatedly cycling through the input from the four sensors.

TDM is commonly used in existing practice, but, as will be described below, the method imposes a severe limitation on the maximum inspection speed, particularly for low frequency ECA probes.

Therefore there exists a need in existing practice for a method of multiplexing which allows improved productivity by achieving a higher inspection speed.

SUMMARY OF THE INVENTION

Accordingly, it is a general objective of the present disclosure to increase the inspection speed in NDT/NDI.

It is further an objective of the present disclosure to increase inspection speed in NDT/NDI by combining Time Division Multiplexing with Pulse-Amplitude Modulation (PAM).

DETAILED DESCRIPTION OF PREFERRED EMBODIMENT

When using TDM, the measurement time is defined as the time taken to perform a complete data acquisition for every sensor. The measurement time determines the rate at which the ECA probe may be physically moved to the next acquisition location, and is therefore the key indicator of inspection speed. The measurement time is affected by the frequency of the excitation signal, the number of time slots (which in existing practice is equal to the number of sensors per electronic input), and an averaging factor, where the averaging factor is the number of excitation cycles to be acquired in every time slot. Averaging is required in order to increase the signal-to-noise ratio (SNR). The measurement time may be expressed by the following equation:

$$\text{measurement time} = \frac{\text{number of time slots} \times \text{averaging factor}}{\text{excitation frequency [Hz]}} \quad (1)$$

The measurement time directly determines the maximum inspection speed. If, for example, an ECA probe has a 1 mm resolution (i.e. it can resolve defects as small as 1 mm), then it is necessary to ensure that at least one complete acquisition is made every time the probe is moved by 1 mm. The maximum speed of motion of the probe is given by:

$$\text{maximum speed} = \frac{\text{probe resolution}}{\text{measurement time}} \quad (2)$$

Thus,

-continued $$\text{maximum speed} = \text{probe resolution} \times \frac{\text{excitation frequency [Hz]}}{\text{number of time slots} \times \text{averaging factor}} \quad (3)$$

Equation (3) defines the dependence of probe motion speed on the excitation frequency and the number of time slots. For example, if the resolution is 1 mm, the excitation frequency is 100 Hz, there are 8 time slots and the averaging factor is 1, then the maximum speed is 12.5 mm/sec.

The maximum speed may be increased by changing the factors in equation (3). However, the probe resolution and the excitation frequency are application-specific and may not be changed, and the averaging factor must be set to preserve an acceptable level of SNR. This leaves little margin to increase the maximum inspection speed, unless the number of successive time slots can be changed or the SNR can be increased.

Figure 2A:
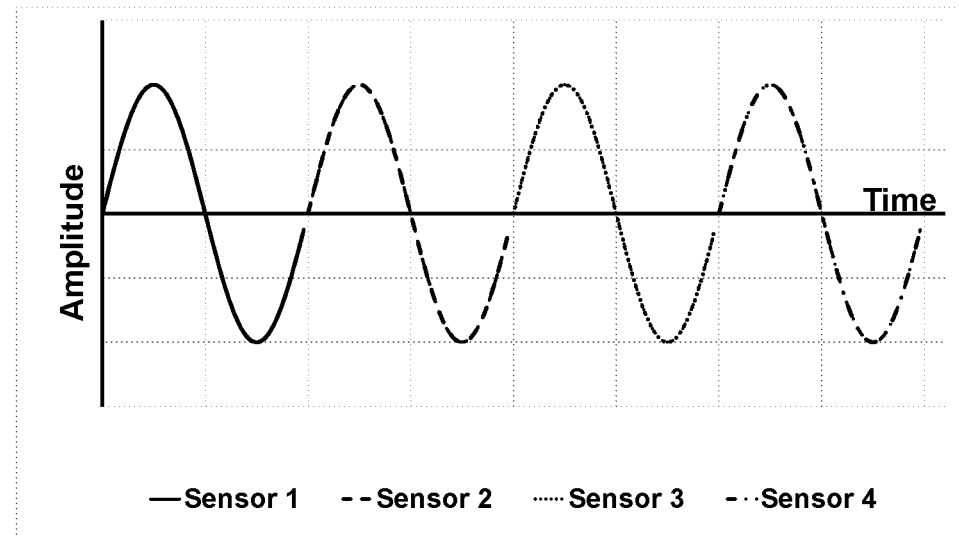
FIG. 2A is an illustrative example of Time Division Multiplexing.
Figure 2B:
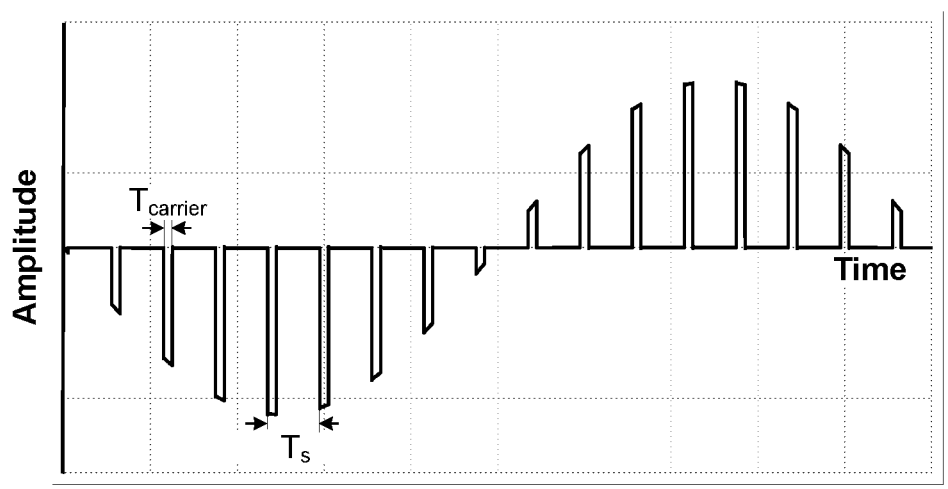
FIG. 2B is a graph showing an example of Pulse-Amplitude Modulation

According to the present invention, the inspection speed is increased by reducing the number of time slots, and this is achieved by combining TDM with Pulse-Amplitude Modulation (PAM). PAM is a form of signal modulation where the message information is encoded in the amplitude of a series of signal pulses. It is an analog pulse modulation scheme in which the amplitudes of a train of carrier pulses are varied according to the sample value of the message signal. FIG. 2B shows pulse-amplitude modulation of a sine wave in which the signal is measured at an electronic input for a carrier time $T_{carrier}$, and measurements are repeated at regular intervals of a sampling period, $T_s$.

The inventors of the present invention have realized that it is possible to increase the maximum inspection speed by a factor equivalent to the number of time slots in existing practice. A key aspect of the present invention is that TDM is used to interleave many PAM samples together (PAM-TDM). As an example, for a probe with 4 time slots, using PAM-TDM would make the inspection speed 4 times faster. This is accomplished by increasing the frequency at which the multiplexer toggles between its input channels, so that channel switching occurs after a shorter multiplexer switching time, $T_{MUX}$. The sampling process of each channel is calculated so that no aliasing occurs, wherein aliasing is an effect that causes different signals to become indistinguishable when sampled. Sampling period, $T_s$, and sampling frequency, $f_s$, respect the following equations (see, for example, Stremler, F. G. (1992), Introduction to Communication Systems, Addison Wesley Longman):

$$T_s \leq \frac{1}{2 \times \text{excitation frequency}} \quad (4a)$$

$$f_s \geq 2 \times \text{excitation frequency} \quad (4b)$$

Equations (4a) and (4b) define a maximum allowable sampling period or minimum sampling frequency for a single sensor. However, the shorter the sampling period or the higher the sampling frequency, the better will be the representation of the input signal. This is known as oversampling.

When PAM sampling is combined with TDM, accounting for multiple sensors requires a shorter multiplexer switching time, $T_{MUX}$, or higher multiplexer switching frequency, $f_{MUX}$. For PAM-TDM, $T_{MUX}$ and $f_{MUX}$ are represented by the following equations:

$$T_{MUX} = \frac{T_s}{\text{Number of sensors}} \quad (5a)$$

$$f_{MUX} = f_s \cdot (\text{Number of sensors}) \quad (5b)$$

Figure 1A:
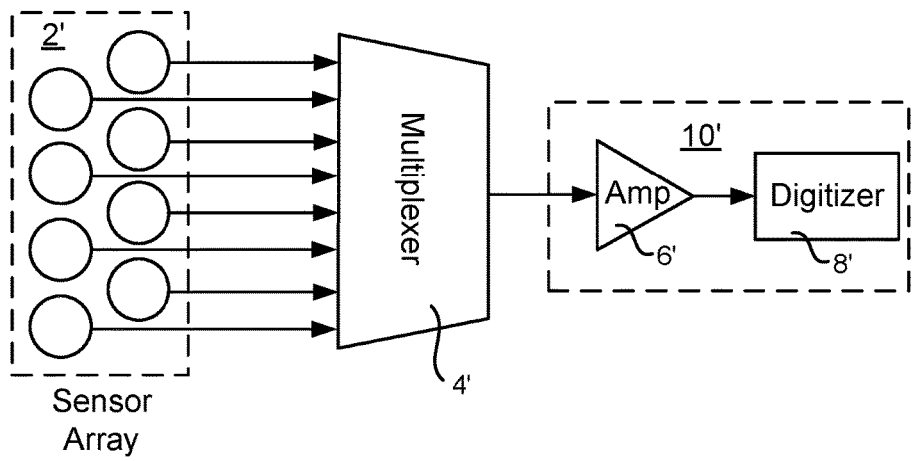
FIG. 1A shows an example of a multiplexer allowing up to eight coils to be scanned with a single sensing input.
Figure 1B:
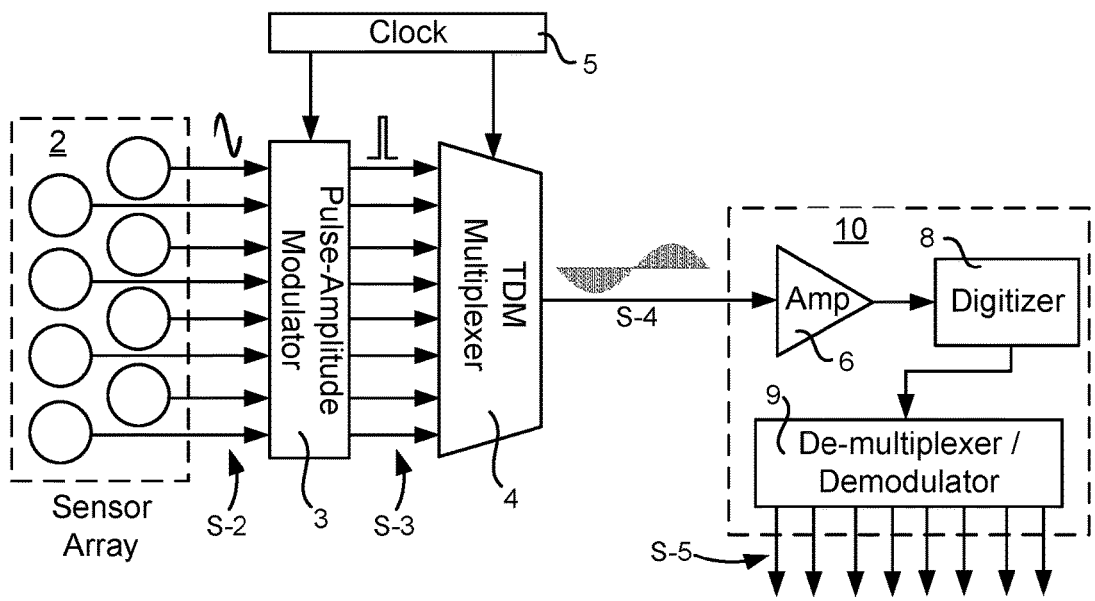
FIG. 1B is a schematic illustration of a combined PAM and TDM circuit according to the present disclosure.

FIG. 1B is a schematic illustration of a PAM-TDM circuit according to the present disclosure. A sensor array 2 produces a multiplicity of sine wave signals S-2, the amplitude and phase of each of sine wave signals S-2 being indicative of flaws in a test object. Sine wave signals S-2 are input to a pulse-amplitude modulator 3 which samples each of sine wave signals S-2 at regular intervals of the sampling period, $T_s$. The output from phase-amplitude modulator 3 is a corresponding multiplicity of pulse signals S-3, where each one of pulse signals S-3 comprises a train of pulses of width $T_{carrier}$, spaced by sampling period $T_s$, and having amplitude corresponding to the amplitude of the corresponding sine wave signal S-2 at the time of sampling. Pulse signals S-3 are input to a TDM multiplexer 4 which scans pulse signals S-3 into a single PAM-TDM signal S-4. A clock 5 controls the timing of both pulse-amplitude modulator 3 and TDM multiplexer 4. PAM-TDM signal S-4 is input to an electronic sensing module 10, comprising an amplifier 6, an optional digitizer 8, and a de-multiplexer/demodulator 9. Note that in the presence of optional digitizer 8, de-multiplexer/demodulator 9 will perform de-multiplexing and the pulse-amplitude demodulation digitally, whereas in the absence of optional digitizer 8, de-multiplexer/demodulator 9 will comprise analog hardware for de-multiplexing and the pulse-amplitude demodulation. The output of de-multiplexer/demodulator 9 is a multiplicity of output pulse signals S-5 wherein the amplitude of each pulse is proportional to the amplitude of corresponding sine wave signals S-2 at their respective sampling times.

Note that pulse-amplitude modulator 3 and TDM multiplexer 4 may be implemented as separate hardware modules or separate integrated circuits. Alternatively, pulse-amplitude modulator 3 and TDM multiplexer 4 may be integrated in a single hardware module or a single integrated circuit. All such implementations of the combination of pulse-amplitude modulator 3 and TDM multiplexer 4 are within the scope of the present disclosure.

It should also be noted that, according to equations (5a) and (5b), TDM multiplexer 4 operates at a multiplexer switching frequency which is greater than the multiplexer switching frequency of existing practice multiplexer 4' by a factor equal to the number of sine wave signals S-2. Similarly, digitizer 8 operates at a frequency which is higher than the frequency of existing practice digitizer 8' by the same factor.

Note that FIG. 1B represents 8 sine wave signals S-2 and 8 corresponding pulse signals S-3 and S-5 for illustrative purposes only. The number of sine wave signals S-2 and corresponding pulse signals S-3 and S-5 can have any value and all values are within the scope of the present disclosure.

Figure 2C:
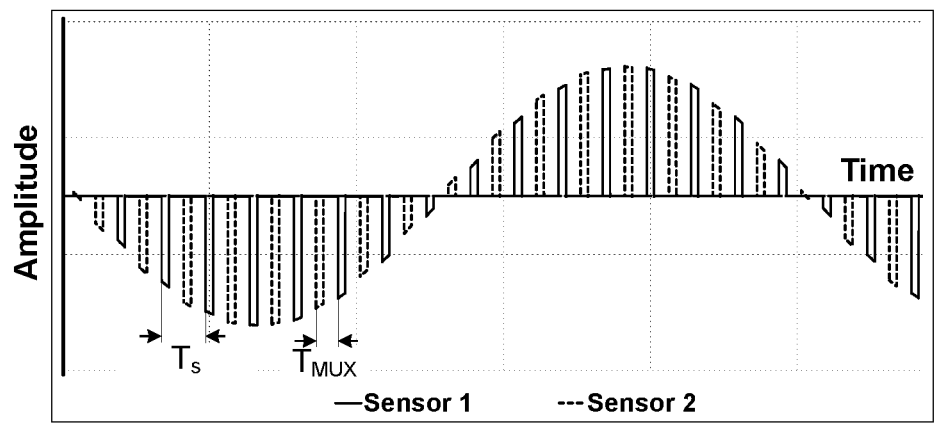
FIG. 2C is a graph showing Pulse-Amplitude Modulation combined with Time Division Multiplexing for two sensors according to the present disclosure.
Figure 2D:
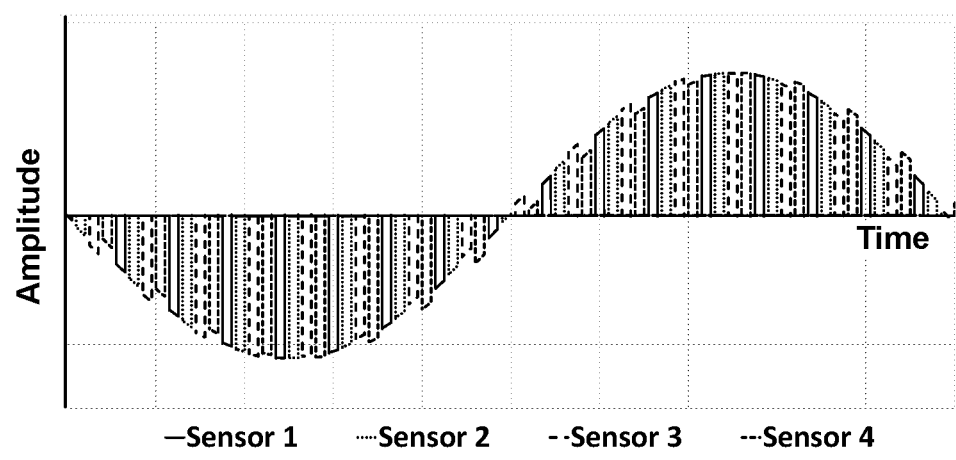
FIG. 2D is a graph showing Pulse-Amplitude Modulation combined with Time Division Multiplexing for four sensors according to the present disclosure.

FIGS. 2C and 2D are graphs showing application of PAM-TDM according to the present disclosure. In both cases oversampling is used to better preserve the shape of the sine wave, and multiplexer switching time, $T_{MUX}$, is short enough to allow 2 channels to be interleaved in FIG. 2C and 4 channels to be interleaved in FIG. 2D. It should be emphasized that FIG. 2D shows interleaved representations of 4 independent signals, and in the case of ECA inputs these signals would be sine waves of different phase and amplitude. It should also be noted that all 4 signals have been sampled within one cycle of the excitation frequency. Sampling with conventional TDM would have required 4 cycles as in FIG. 2A and the time taken for the sampling would have been four times longer.

In an exemplary embodiment of the present invention, the excitation frequency may be 1000 Hz, and the multiplexer may have 4 input channels. In this case the maximum sampling period given by equation (4a) is 500 us, and an exemplary sampling period, $T_s$, is 60 us corresponding to oversampling by a factor of 8.3. From equation (5a), multiplexer switching time, $T_{MUX}$, is 15 us.

The number of channels that can be interleaved depends on the sampling rate of digitizer 8. The speed at which the multiplexer can switch a signal could also be a limiting factor. Thus, both multiplexer 4 and digitizer 8 must be chosen so that their specifications will meet the requirements for $T_{MUX}$ and $T_s$.

Interleaving multiple PAM samples has an impact on the quality of the acquired signal, because chopping the signal into finite samples will degrade its SNR. Although loss of SNR is a necessary consequence of interleaving multiple PAM signals, use of an oversampling digitizer may compensate for the loss of SNR. Although there is a technological limit to available digitizer sampling frequency, PAM-TDM for ECA is of interest mostly at lower frequencies, and therefore digitizer oversampling at available sample frequencies may result in significant SNR improvement. The expected reduction in SNR due to interleaving can be approximated by the following relation:

$$SNR \text{ reduction} = 10 \log\left(\frac{1}{\text{number of interleaved channels}}\right) \quad (6)$$

For an 8-channel system, this would yield:

$$SNR \text{ reduction}=10 \log(\tfrac{1}{8}) \rightarrow SNR \text{ reduction}=-9 \text{ dB} \quad (7)$$

In order to compensate for the SNR reduction of equation (7), the digitizer should be chosen so that its sampling frequency is 8 times faster. For instance, if an ECA instrument is designed around a 10 MHz digitizer, an equivalent PAM-TDM instrument would use an 80 MHz digitizer.

The PAM-TDM method of the present invention has a number of significant advantages over conventional TDM for ECA inspection. The most important advantage is that the inspection speed can be dramatically increased, especially at lower ECA signal frequencies. The factor of increase in speed is essentially equal to the number of input channels and is due to the fact that ECA signal treatment can be performed simultaneously on all input channels, rather than being processed time slot by time slot as in existing practice.

Figure 3:
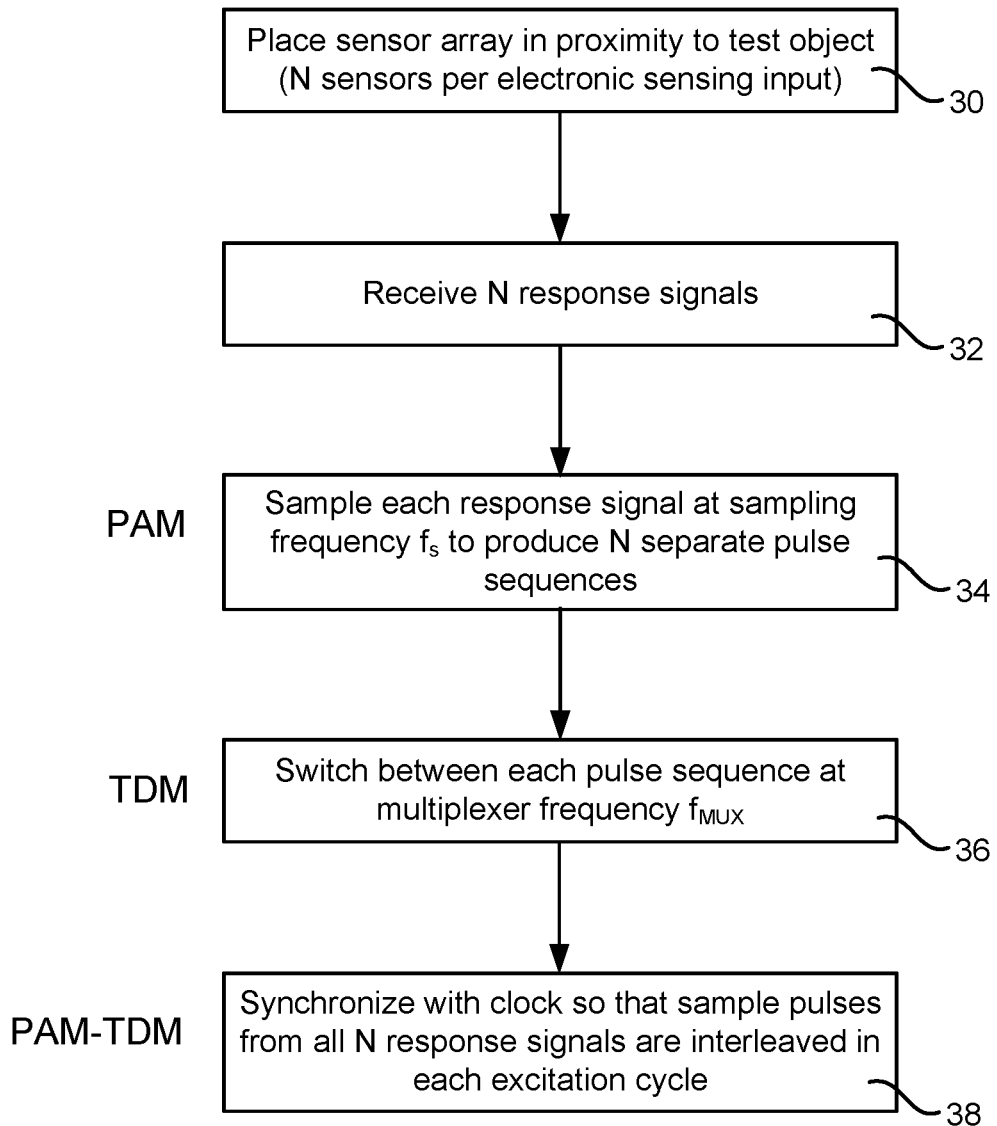
FIG. 3 is a schematic illustration of an inspection method according to the present disclosure.

FIG. 3 illustrates a method according to the present disclosure. In step 30 the sensor array is placed in proximity to the test object, wherein there are N sensors per electronic sensing input. In step 32, N response signals are received, one from each of the N sensors. Step 34 is the PAM step in which each of the response signals is sampled at sampling frequency $f_s$ to produce N separate pulse sequences. Step 36 is the TDM step in which the multiplexer switches between each of the N separate pulse sequences. In step 38, clock 5 synchronizes the sampling time, the sampling frequency and the multiplexer frequency so that sample pulses from all N response signals are interleaved in each excitation cycle.

Although the present invention has been described in relation to particular embodiments thereof, it can be appreciated that various designs can be conceived based on the teachings of the present disclosure, and all are within the scope of the present disclosure.

What is claimed is:

1. A data acquisition circuit for non-destructive testing (NDT) of a test object, the circuit comprising: a multiplicity of N sensors, producing a corresponding multiplicity of N response signals indicative of flaws in the test object; a pulse-amplitude modulator for sampling sample amplitudes of each one of the multiplicity of N response signals at periodic sampling times repeated at a sampling frequency, and producing a corresponding multiplicity of N input pulse sequences for each one of the multiplicity of N response signals, wherein the amplitude of each pulse in each one of the multiplicity of N input pulse sequences is equal to the sample amplitude at a corresponding sampling time; a time division multiplexer having N multiplexer inputs for the N input pulse sequences and switching at a multiplexer frequency between each of the N input pulse sequences such that the N input pulse sequences are interleaved into a single multiplexed sequence of pulses; and, a clock for synchronizing the sampling times, the sampling frequency and the multiplexer frequency, wherein the non-destructive testing is eddy current testing and the multiplicity of sensors is a multiplicity of eddy current sensors.

2. The circuit of claim 1 wherein the pulse-amplitude modulator and the time division multiplexer are implemented in separate integrated circuits.

3. The circuit of claim 1 wherein the pulse-amplitude modulator and the time division multiplexer are implemented in a single combined integrated circuit.

4. The circuit of claim 1 wherein the multiplexed sequence of pulses is input to an electronic sensing module having a single input, the electronic sensing module comprising a de-multiplexer/demodulator configured to output N output pulse sequences, wherein the amplitude of each pulse in each of the N output pulse sequences is proportional to the sample amplitude of a corresponding pulse of a corresponding one of the N input pulse sequences.

5. The circuit of claim 4 wherein the output pulse sequences are analog signals.

6. The circuit of claim 4 wherein the electronic sensing module further comprises a digitizer and the output pulse sequences are digital signals.

7. The circuit of claim 1 wherein the sensors are physically moved to a sequence of test positions and reside at each test position for a measurement time.

8. The circuit of claim 7 wherein the sensors are excited by an excitation signal having an excitation frequency, wherein the measurement time is equal to an averaging factor divided by the excitation frequency, and wherein the sampling frequency is greater than twice the excitation frequency.

9. The circuit of claim 8 wherein the sampling frequency is greater than N times the excitation frequency.

10. The circuit of claim 8 wherein the multiplexer frequency is equal to N multiplied by the sampling frequency.

11. A method for non-destructive testing (NDT) of a test object, the method comprising the step of: placing a multiplicity of N sensors in proximity to the test object; acquiring a corresponding multiplicity of N response signals indicative of flaws in the test object; sampling sample amplitudes of each one of the multiplicity of N response signals at periodic sampling times repeated at a sampling frequency; producing a corresponding multiplicity of N input pulse sequences for each one of the multiplicity of N response signals, wherein the amplitude of each pulse in each one of the multiplicity of N input pulse sequences is equal to the sample amplitude at a corresponding sampling time; switching at a multiplexer frequency between each of the N input pulse sequences; and, synchronizing the sampling times, the sampling frequency and the multiplexer frequency such that the N input pulse sequences are interleaved into a single multiplexed sequence of pulses, wherein the non-destructive testing is eddy current testing and the multiplicity of sensors is a multiplicity of eddy current sensors.

12. The method of claim 11 further comprising the step of inputting the multiplexed sequence of pulses to a de-multiplexer/demodulator configured to output N output pulse sequences, wherein the amplitude of each pulse in each of the N output pulse sequences is proportional to the sample amplitude of a corresponding pulse of a corresponding one of the N input pulse sequences.

13. The method of claim 12 wherein the output pulse sequences are analog signals.

14. The method of claim 12 wherein the output pulse sequences are digital signals.

15. The method of claim 11 wherein the sensors are physically moved to a sequence of test positions and reside at each test position for a measurement time.

16. The method of claim 15 wherein the sensors are excited by an excitation signal having an excitation frequency, wherein the measurement time is equal to an averaging factor divided by the excitation frequency, and wherein the sampling frequency is greater than twice the excitation frequency.

17. The method of claim 16 wherein the sampling frequency is greater than N times the excitation frequency.

18. The method of claim 16 wherein the multiplexer frequency is equal to N multiplied by the sampling frequency.

* * * * *